United States Patent [19]
Wilbur et al.

[11] Patent Number: 5,102,651
[45] Date of Patent: Apr. 7, 1992

[54] PROCESS FOR ISOLATION AND RADIOLABELING OF PHARMACEUTICALS WITH ISOTOPES OF ASTATINE

[75] Inventors: Daniel S. Wilbur, Edmonds; Stephen W. Hadley, Seattle, both of Wash.

[73] Assignee: NeoRx Corporation, Seattle, Wash.

[21] Appl. No.: 459,066

[22] Filed: Dec. 29, 1989

[51] Int. Cl.$^5$ .............................................. A61K 43/00
[52] U.S. Cl. ...................................... 424/1.1; 423/249
[58] Field of Search .......................... 424/1.1; 423/249

[56] References Cited

U.S. PATENT DOCUMENTS

| | | | |
|---|---|---|---|
| 4,681,727 | 7/1987 | Mirzadeh et al. | 423/249 X |
| 4,826,672 | 5/1989 | Milius et al. | 424/1.1 |
| 4,870,188 | 9/1989 | Wilbur et al. | 424/1.1 X |
| 4,876,081 | 10/1989 | Wilbur et al. | 424/1.1 |
| 4,885,153 | 12/1989 | Wilbur et al. | 424/1.1 |
| 4,894,218 | 1/1990 | Engelstad et al. | 424/1.1 |

FOREIGN PATENT DOCUMENTS 203764  12/1986  European Pat. Off. .

OTHER PUBLICATIONS

Wilbur et al., *Radiochimica Acta*, 47, 137–142, (1989), "Reactions of Organometallic Compounds with Astatine-211, Application to Protein Labeling".

Shiue, C.-Y., and Wolf, A. P., *Journal of Labelled Compounds and Radiopharmaceuticals*, vol. XVIII, No. 7, pp. 1059–1066, "Synthesis of 4-fluoro-2,3-dimethyl-1-phenyl-3-pyrazoline-5-one (4-fluoroantipyrine) and $^{18}$F-Labeled analog by direct fluorination of antipyrine with molecular fluorine".

*Primary Examiner*—John S. Maples
*Attorney, Agent, or Firm*—Kathryn A. Seese

[57] ABSTRACT

A process for recovering At-211 from a target and simultaneously producing an At-211-labeled radiopharmaceutical agent involves introducing volatilized At-211, produced by dry distillation of an irradiated Bi-209 target, into a solution containing a compound that binds the At-211 to form an At-211-labeled radiopharmaceutical agent. The radiopharmaceutical agent may have therapeutic use as is, or may be attached to a targeting protein such as an antibody prior to administation to a patient.

23 Claims, 8 Drawing Sheets

TABLE I

| Distillation # | 1 | 2 | 3 | 4 | 5 | 6 | 7 | 8 | 9 | 10 |
|---|---|---|---|---|---|---|---|---|---|---|
| Temperature | 250-430 | 400-650 | 600-660 | 625-680 | 710-720 | 665-700 | 600-650 | 700-715 | 710-730 | 700-730 |
| Charcoal Trap | <1% | — | <1% | <1% | <1% | <1% | <1% | 1% | 1% | 3% |
| Distilling Tube | 6% | — | 2% | <1% | 1% | <1% | 1% | <1% | 1% | 5% |
| Target and Boat | 68% | — | 24% | 18% | 11% | 30% | 21% | 15% | 17% | 13% |
| Reaction Vessel (bottom) | 25% | 50% | 70% | 66% | 79% (60%) | 60% | 74% (61%) | 82% (81%) | 75% (72%) | 77% (44%) |
| Trap #2 | <1% | — | 4% | 13% | 6% | 10% | 2% | <1% | <1% | <1% |
| Trap #3 | NA | NA | NA | 4% | 2% | <1% | <1% | <1% | <1% | <1% |

PROCESS FOR ISOLATION AND RADIOLABELING OF PHARMACEUTICALS WITH ISOTOPES OF ASTATINE

BACKGROUND OF THE INVENTION

Radionuclides which emit high LET particulate radiation (e.g., alpha particles) are very attractive for use as therapeutic radiopharmaceutical agents. Alpha particles are extremely radiotoxic to cells. Recent advances in the chemistry of labeling small organic molecules with astatine-211 have prompted renewed interest in this isotope. Astatine-211 with a half-life of 7.2 hours has excellent radiation characteristics, decaying with 42% of an alpha emission at 5.87 MeV and 58% decay by electron capture. The electron capture decay daughter, pollonium-211, is very short-lived (0.5 seconds) with an alpha emission at 7.45 MeV. Thus alpha emission is associated with 100% of the decays of astatine-211.

Due to the short half-life and high cost of astatine-211, its commercial application will require the use of a method for radiolabeling which is rapid and efficient. Additionally, consideration of the labeling personnel's safety must be of paramount concern as astatine-211 is an alpha emitting radionuclide.

Astatine-211 is a cyclotron produced radioisotope. Irradiation of a bismuth-209 target with a 28 MeV alpha beam affords astatine-211 by the alpha,2n reaction. Problems associated with the recovery of astatine from the bismuth targets have been a limitation on the development of astatine-211 radiopharmaceuticals. The most common method for recovering the astatine from a bismuth target is distillation. Astatine can be distilled from bismuth targets by heating the targets at temperatures above 600° C. in a quartz tube furnace. A carrier gas sweeps through the furnace and the volatile astatine is then trapped using a variety of techniques. The most common techniques for trapping astatine are dissolution of the astatine in different solvents or adsorbing the astatine onto various surfaces such as platinum disks or silica gel. Recoveries using these methods can be highly variable.

Dissolution of the astatine by bubbling the carrier gas stream into a solvent generally is not an efficient process. In order to obtain an acceptable recovery of the astatine, a gas bubbler apparatus containing a fairly large volume of solvent is generally required. A variety of solvents have been used including water, sulfuric acid, 0.1N sodium sulfite, nitric acid/potassium dichromate solution, chloroform and methanol. Some of these solvents are not compatible with labeling of organic radiopharmaceuticals. Also, in many instances the solution concentration of astatine is quite low and a concentration step or solvent exchange step is thus required prior to labeling. Further, depending upon conditions, some of the trapped astatine can react with impurities in the solvent.

Adsorption of the astatine onto metal surfaces such as platinum is an efficient process. However a second processing step (typically a distillation) is required before the astatine can be used for labeling. Adsorption onto silica gel is another method for trapping astatine, which is then eluted from the silica gel bed using various solvents. Unfortunately, often only about 50% of the trapped astatine can be recovered from the silica gel by elution with 0.1N NaOH or sodium bisulfite solution. The volume required for maximal recovery can be prohibitively large for the efficient reaction in a subsequent step to radiolabel a molecule.

Common to most of the above methods is the requirement of secondary processing steps, e.g., distillation, concentration, solvent exchange etc., to obtain the astatine for labelling of radiopharmaceuticals. The time required for this secondary processing contributes to the overall loss of astatine from decay of the isotope. With a half-life of 7.2 hr, 9.2% of the astatine-211 is lost per hour. Significant improvements are possible if one could eliminate or combine several of the steps involved with the recovery of the isotope.

SUMMARY OF THE INVENTION

The present invention provides a process for producing an At-211-labeled radiopharmaceutical compound, comprising:

vaporizing At-211 from an irradiated bismuth metal target, and introducing the vaporized At-211 into a solution comprising a compound that binds the At-211 to form an At-211-labeled radiopharmaceutical compound.

The At-211 is thus recovered from the target in the form of a radiopharmaceutical compound. The radiopharmaceutical compound may have therapeutic use as is, or may be attached to another molecule such as an antibody prior to administration to a patient.

The At-211 is preferably vaporized by dry distillation. To enhance safety, the inventive process advantageously is carried out within a single enclosed apparatus, preferably under vacuum.

BRIEF DESCRIPTION OF THE FIGURES

In FIG. 1, "A" represents teflon tubing, 15 cm × 0.8 mm i.d. × 1.6 mm o.d. fitted on one end with a ¼-28 threaded polypropylene bushing. "B" represents a coupling, ¼-28 threaded polypropylene. "C" represents a tefzel adapter, ¼-28 thread to female luer adapter.

DETAILED DESCRIPTION OF THE INVENTION

The present invention provides a process which is rapid, highly efficient, and safe for isolation of astatine isotopes from an irradiated bismuth metal. The process of the invention permits the direct preparation of At-211 labeled radiopharmaceutical agents.

The process of the present invention for producing an At-211-labeled radiopharmaceutical compound comprises:

vaporizing At-211 from an irradiated bismuth metal target, and introducing the vaporized At-211 into a solution comprising a compound that binds the At-211 to form an At-211-labeled radiopharmaceutical compound.

Currently, processing of a bismuth target containing astatine into a radiopharmaceutical generally involves the multiple-step procedures described above. The process of the present invention improves the overall recovery of astatine by combining several of the steps into a single operation. The At-211 that is released from the bismuth is immediately introduced into a solution of reagent(s) which "chemically traps" the astatine as the desired radiopharmaceutical. Thus, separate steps for trapping (recovering) the At-211, followed by reaction(s) to produce the desired radiopharmaceutical compound, (with intermediate steps, e.g., distillation or the exchange or concentration of solvents, often being required) are not necessary in the present method. The efficient production of At-211-labeled compounds achieved by the inventive process is especially important in view of the relatively short half life of At-211.

Figure 1:
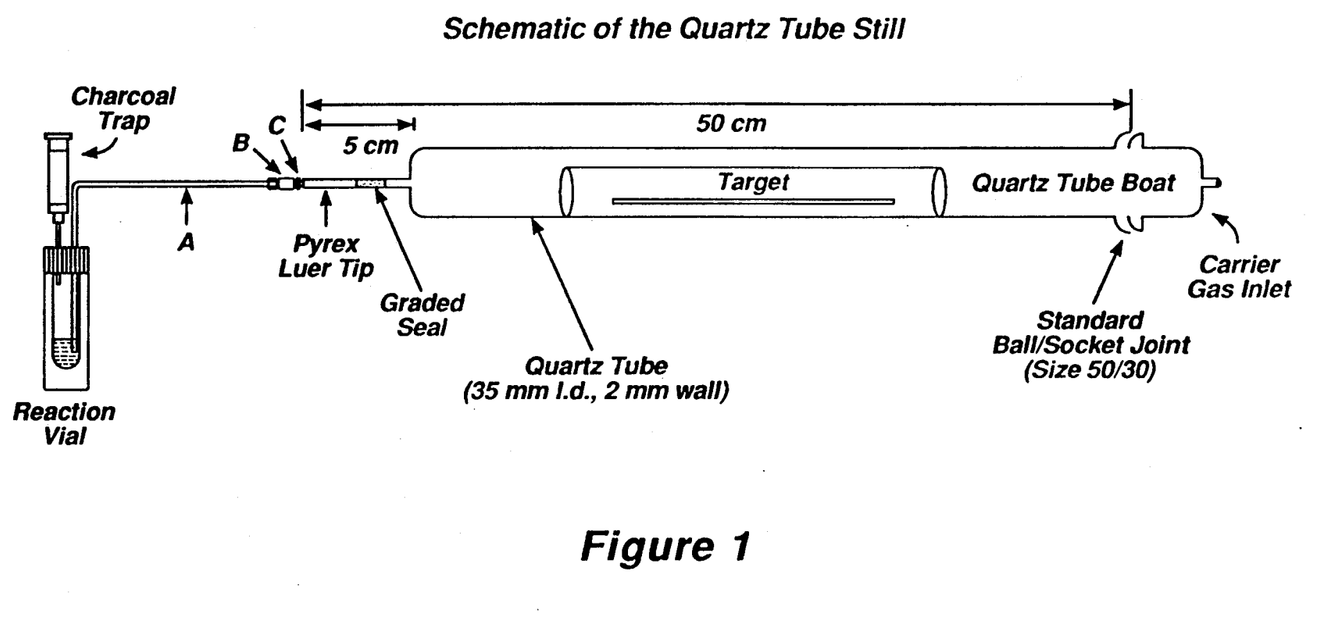
FIGS. 1 and 3 each depict an enclosed apparatus suitable for use in the process of the invention.
Figure 3:
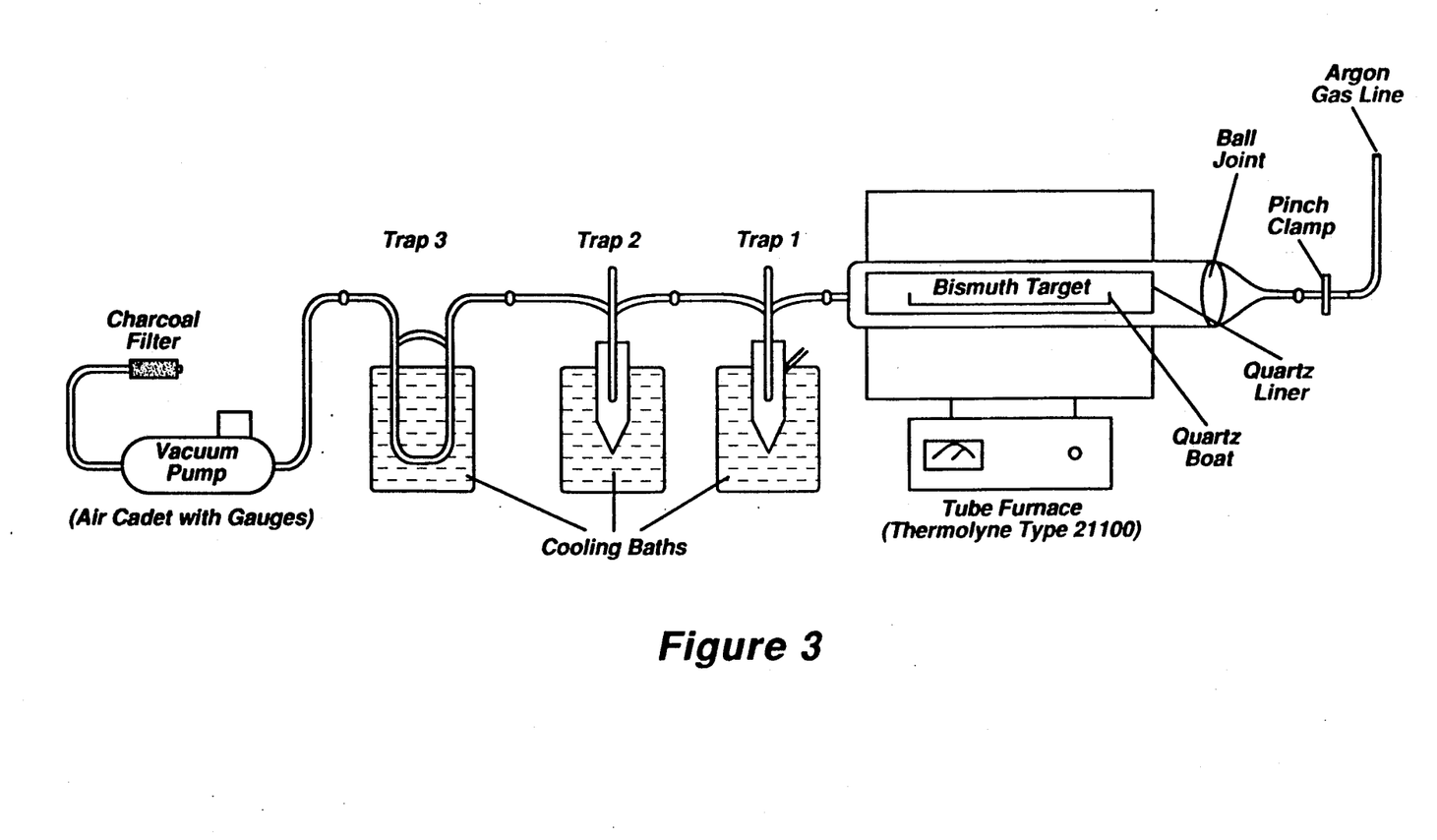

For purposes of enhanced safety and recovery of At-211, the entire process is preferably conducted in a single enclosed apparatus (advantageously charcoal-filtered). Examples of suitable apparatuses are depicted in FIGS. 1 and 3. Concerns about the safety of handling astatine also highlight an advantage of this improved method for recovering astatine. One of the most common ways to ingest astatine is by inhalation of its vapors. Handling of volatile elemental astatine is to be avoided if at all possible. By using the method of the present invention, the astatine vapor is rapidly trapped as a less volatile radiopharmaceutical agent. One can largely avoid having to handle the astatine in its volatile form, since the astatine is either in the form of the radiopharmaceutical reagent or reduced to astatide when removed from the enclosed apparatus.

Bismuth metal may be irradiated to produce At-211 by conventional procedures. In general, Bi-209 is irradiated with a 28 MeV alpha beam in a cyclotron to produce At-211.

The At-211 may be released from the irradiated bismuth target by any suitable procedure. The relatively volatile At-211 may be vaporized to release it from the target. A preferred procedure is dry distillation, whereby the At-211 is released in the vapor phase from the target. In one embodiment of the invention, the At-211 is distilled from the target by heating the target to a temperature of from about 650° to 750° C. for about 10 to 60 minutes, with about 10-15 minutes at 700°-720° C. generally being sufficient. The dry distillation advantageously is conducted in a pre-dessicated enclosed apparatus under vacuum.

The vaporized At-211 then is introduced into a solution containing a compound that binds the At-211 to form an At-211-labeled radiopharmaceutical compound. The At-211 is introduced into the solution in presumably elemental form immediately after release from the target, i.e., without any intermediate procedures for trapping the At-211.

The At-211 may be introduced into the solution by sweeping a carrier gas through the apparatus such that the vaporized At-211 is carried to a vessel containing the solution. The carrier gas may be any suitable inert gas such as nitrogen or, preferably, argon. The solution may be contained in a cooled vessel such as a dry ice/isopropanol cooled trap, in which the At-211-containing gas is condensed onto the solution. Alternatively, the At-211-containing carrier gas may be bubbled through the solution. For consistent recoveries, a preferred alternative to the use of a carrier gas is to allow the vaporized At-211 to be swept under vacuum to the solution, and condensed thereon.

The solution contains one or more compounds that bind the astatine to form an At-211-labeled radiopharmaceutical compound. The At-211 is thus chemically trapped in the solution in the form of a useful radiopharmaceutical reagent.

The term "At-211-labeled radiopharmaceutical compound" as used herein refers to an At-211-labeled compound that is itself useful as a therapeutic radiopharmaceutical agent, or that may be attached to another molecule to form a therapeutic radiopharmaceutical agent. In other words, the radiopharmaceutical compound formed in the solution is at least a component of a therapeutically effective radiopharmaceutical having in vitro or in vivo medical use. Thus, it is not necessary to transfer the At-211 from the compound that binds it in the solution to any other compound to form a useful radiopharmaceutical agent.

The compound(s) in the solution may be any compounds that bind At-211 to form a useful radiopharmaceutical. Compounds that efficiently bind At-211 generally are organic compounds that contain a highly reactive organometallic functionality (preferably substituted directly on an aromatic ring or on a vinyl group) which increases the rate of reaction and causes the reaction to occur in a site specific manner. Examples of suitable organometallic functionalities include, but are not limited to, tri-alkyl tin and tri-alkyl germanium groups (e.g., tri-n-butyl tin and tri-methyl germanium) and phenyl rings having mercury or boron substituted directly thereon. One reactive organometalic group is of the formula:

wherein each of $R_1$, $R_2$, and $R_3$ is an alkyl group of from 1 to about 6 carbon atoms. Examples of astatine-binding molecules comprising such organometallic groups are presented by Wilbur et al. in *Radiochimica Acta*, 47, 137–142 (1989).

In one embodiment of the invention, the compound may be a drug or derivative thereof. The At-211-labeled drug may be used in combination therapy, wherein both the drug and the radiolabel attached thereto exert a therapeutic effect. If a drug does not comprise a reactive functionality that will efficiently bind At-211, then the drug may be derivatized with such a functionality (e.g., one of the organometallic groups described above) at a site that does not eliminate the drug's therapeutic activity. Examples of drugs that may be derivatized and used to bind At-211 include but are not limited to anti-viral agents, anti-neoplastic drugs, other chemotherapeutic agents, and receptor-binding compounds such as steroids, dopamine or other neuroleptic receptor binding drugs.

Another type of compound that may be used to bind At-211 is a protein labeling reagent. Such reagents comprise a conjugation group, which is a functional group that will react with a protein to bind the reagent thereto. The At-211-labeled radiopharmaceutical compound formed in the solution is attached to a protein (advantageously in the same enclosed apparatus) prior to use. Alternatively, the reagent may already be attached to a protein when added to the solution, so that binding of At-211 by the reagent produces an At-211-labeled protein in the solution.

Proteins contain a variety of functional groups that are available for reaction with a suitable conjugation group on a radiopharmaceutical compound to bind the compound to the protein. For example, an active ester group on the radiopharmaceutical compound will react with an epsilon amine on a lysine residue of a protein to form an amide bond. Preferred active esters include succinimidyl esters, phenolic esters such as 2,3,5,6,-tetrafluorophenyl ester, and thiophenol esters such as 2,3,5,6,-tetrafluorothiophenyl ester. Alternatively, the protein and/or compound may be derivatized to expose or attach additional reactive groups.

The derivatization may involve any of a number of linker molecules such as those available from Pierce Chemical Company, Rockford, Illinois. Alternatively, the protein derivatives may be produced by chemical treatment of the protein (which may be an antibody). Procedures for generation of free sulfhydryl groups on antibodies are known. Maleimide protein conjugation groups on a radiopharmaceutical compound are reactive with the sulfhydryl groups. When the protein is a carbohydrate, derivatization may involve chemical treatment of the carbohydrate, e.g., glycol cleavage of the sugar moiety of a glycoprotein antibody with periodate to generate free aldehyde groups. The aldehydes are reactive with primary amine or hydrazine groups on a radiopharmaceutical compound.

The protein may be a targeting protein that binds to a desired target site, thus delivering the At-211 to the target site. The targeting protein may bind to a receptor, substrate, antigenic determinate, or other binding site on a target cell or other target site. Examples of targeting proteins are antibodies, hormones, enzymes, biologic response modifiers, and variants thereof produced through genetic or protein engineering.

In one embodiment of the invention, the targeting protein is a monoclonal antibody that binds to cancer cells. Among the many such monoclonal antibodies are anti-TAC or other interleukin-2 receptor antibodies; 9.2.27 and NR-ML-05, reactive with the 250 kilodalton human melanoma-associated proteoglycan, and a pancarcinoma antibody designated NR-LU-10. The antibody employed may be an intact whole antibody or a fragment thereof, such as a Fab, Fab', F(ab,)$_2$, or F$_v$ fragment produced by conventional means or by genetic or protein engineering techniques.

One suitable protein labeling reagent comprising a vinyl group is described in U.S. Pat. Nos. 4,870,188 and 4,876,081, which are hereby incorporated by reference in their entirety. Another example of a protein labeling reagent that may be used to bind At-211 in accordance with the present invention is a reagent of the following formula:

R—Ar—R' wherein
R represents an organometallic group;
Ar represents an aromatic or heteroaromatic ring;
and R' represents a short chain substituent that does not highly activate the ring Ar toward electrophilic substitution, and which comprises a protein conjugation group.

Reagents of this formula are described in more detail, along with procedures for the preparation thereof, in European patent application publication number 203,764 and in copending U.S. patent application Ser. No. 07/338,497, now U.S. Pat. No. 4,885,153, both of which are hereby incorporated by reference in their entirety. The organometallic group may be of the formula —SN—R$_3$, wherein each of the three R groups is a lower alkyl group of from 1-6 carbon atoms. Examples of suitable R' substituents are —(CH$_2$)''—Q and —CONH—(CH$_2$)''—Q wherein Q represents a protein conjugation group. The spacer —(CH$_2$)''— can be a straight or branched chain alkyl or heteroalkyl group containing up to 12 but preferably no more than 5 straight-chain carbon atoms. Most preferably, n represents an integer from 0–3.

Examples of radiopharmaceutical compounds produced upon binding of At-211 by such compounds are:

or wherein n and Q are as described above. These radiopharmaceutical compounds are attached to a protein to form an At-211-labeled protein having therapeutic use.

At-211-binding compounds comprising chemically reactive conjugation groups may be attached to molecules other than proteins, either before or after radiolabeling. For example, a compound comprising an active ester may be reacted with a drug having a primary amine group outside the drug's active site, thereby attaching the compound to the drug. Examples of such drugs are the anti-cancer agents doxorubicin and daunorubicin, which comprise a sugar moiety bearing a primary amine group. Certain drugs are known to target specific sites or tissues in vivo.

Other molecules to which the At-211-binding compound may be attached include those that target undesired components of blood. The resulting At-211-labeled compounds may be used to treat such disorders as leukemia or to destroy viruses and other contaminants in blood, either in vivo or in vitro (e.g., prior to transfusion). Other useful targeting molecules are those that target anti-rejection molecules. Targeting molecules may bind to cells, proteins, peptides, or other components associated with a desired target site.

The compound that binds At-211 may be attached to an insoluble support material in the solution. In one embodiment of the invention, the attachment is such that binding of At-211 releases the At-211-labeled radiopharmaceutical from the insoluble support, whereas the unlabeled form of the compound remains attached to the support. The desired radiopharmaceutical is thus easily separated from the unlabeled compound, e.g., by filtration of the reaction mixture.

Suitable insoluble support materials include agarose, cellulose, latex, and other polymers, for example. The polymers may be derivatized with (or activated to contain) a functional group reactive with a desired astatine-binding compound to attach the compound to the support. Such polymers containing reactive groups are known.

Other compounds suitable for use in the process of the present invention are described in U.S. Pat. No. 4,826,672, which is hereby incorporated by reference in its entirety. These compounds may be represented by the general formula:

wherein $R_1$, $R_2$, and $R_3$ are each independently selected from aryl and alkyl groups having less than 10 carbon atoms, and Z comprises an unsaturated organic component. In one embodiment of the present invention, $R_1$, $R_2$, and $R_3$ are each selected from alkyl groups of 1-6 carbon atoms. The organometallic group therefore may be a trimethylstannyl or tributylstannyl group, for example. Reaction with At-211 produces radiopharmaceuticals of the formula (At-211)-Z.

Z may, for example, include a steroidal group, a vinyl group, or an aryl group. Preferred aryl groups include antibody-coupling aryl groups such as benzoic acid or substituted benzoic acid, other carboxylic acids, aromatic amines, aromatic isocyanates, or aromatic isothiocyanates. Z also may represent a styrene or polymer thereof.

Among these compounds are 4-tri-n-butylstannyl benzoic acid oxazoline (which binds At-211 to form p-astatobenzoic acid, a protein labeling reagent) and 3-tri-n-butylstannyltamoxifen (which binds At-211 to form 3-astatotamoxifen, an At-211-labeled anti-neoplastic drug). Other drug derivatives, e.g., trialkylstannylated vinyl estradiols and steroids, may be employed as the compound that binds astatine.

The desired astatine-binding compound is dissolved in a compatible solvent. At-211 is reacted with the compound in the solution under conditions that allow or promote binding of the At-211 by the compound. The solution may comprise two or more such compounds, as well as other reagents. For example, an oxidizing agent may be used to oxidize At- to At+, thereby producing a more reactive species of astatine. The oxidizing agent should be relatively gentle to avoid undesirable reaction with the organometallic group or other groups on the astatine-binding compound. Relatively gentle organic oxidizing agents such as N-chlorosuccinimide, chloramine-T, perbenzoic acid, or hydrogen peroxide may be included in the solution.

Thus, the present invention in one embodiment provides a process for recovering At-211 as a radiopharmaceutical compound from an irradiated bismuth metal target. The process involves placing the irradiated target into an enclosed apparatus, then heating the target for about 10-60 minutes at a temperature of from about 650° to 750° C., thereby vaporizing the At-211 from the target. Heating at 700°-720° C. for about 10-15 minutes is generally sufficient.

The vaporized At-211 is condensed onto a solution comprising an oxidizing agent and a compound that binds the At-211 to form an At-211-labeled radiopharmaceutical compound. The radiopharmaceutical is recovered by any suitable means, depending on the particular compound. The radiopharmaceutical may be attached to another molecule such as a drug or targeting protein prior to recovery.

In one embodiment, the inventive method disclosed herein is conducted in an apparatus that allows a dry distillation of astatine-211 to be accomplished within 10-15 minutes to give 70-90% recovery. As the astatine is distilled it is condensed onto a cooled solution containing a mild oxidizing agent (e.g. N-chlorosuccinimide) to form a reactive species of astatine. The solution also contains an organic compound, preferably comprising an organometallic functionality (e.g. aryltri-n-butyltin) present for electrophilic substitution (exchange) with the astatine. Using this method, the entire process of labeling with astatine-211 may be oompleted in 20-30 minutes and yields of 50-90% of the astatine-211 as the labeled radiopharmaceutical compound are achieved. The At-211 is thus recovered from an irradiated target, and a useful radiopharmaceutical agent is produced, in a single operation.

The method of the present invention provides a number of advantages. Improvements in the overall percent recovery of astatine-211 from a bismuth-209 target are achieved for several reasons. One reason is shortening of the time required to process the astatine into the radiopharmaceutical, thus reducing losses attributable to decay. Additionally, a single operation replaces the two or three operations commonly required in currently used procedures. For example, if a single operation takes one hour to complete and affords an 85% yield of the desired product, a three step operation would require an average overall efficiency of 95% for each step to achieve an equivalent efficiency in the same period of time.

The chemical form or oxidation state of the recovered astatine is always an issue when the material is recovered by distillation. Oxidation of astatine(0) (elemental) to higher oxidation states during the distillation and recovery process may render the astatine unreactive and unsuitable for further chemical transformations. Characterization of the chemical nature of the astatine recovered is not a trivial task. In the method of the present invention, the astatine is recovered directly as the radiopharmaceutical agent, which is more easily characterized.

The following examples are provided to illustrate certain embodiments of the invention, and are not to be construed as limiting the scope of the invention disclosed and claimed herein.

EXAMPLE 1

Preparation of a para-astato-phenvl N-succinimidyl ester Protein Labeling Reagent The procedure followed in this example may be summarized as follows:

1

-continued

2

Compound 1, N-succinimidylpara-(tri-n-butylstannyl) benzoate, was prepared as described in European patent application publication number 203,764, which is hereby incorporated by reference in its entirety.

The distillation apparatus was assembled as depicted in FIG. 1. The quartz distillation tube is inside an oven. The reaction vial was removed from the quartz distillation tube by disconnecting the Tefzel ¼-28 thread to female Luer adapter from the Pyrex Luer tip of the still. Into the reaction vial was placed N-succinimidyl para-tri-D-butylstannylbenzoate (1) (100 ug in 100 uL 1% HOAc/MeOH, 0.20 umol), N-chlorosuccinimide (NCS) (80 ug in 80 uL MeOH, 0.60 umol), 5% HOAc/MeOH (400 uL), and phosphate buffered saline (PBS) (50 uL). The furnace was turned on and allowed to equilibrate at 700° C. under a stream of argon gas for approximately 30 min. During the equilibration process the argon gas was allowed to pass through the heated still and exit into the glove box environment.

The reaction vial was reconnected to the equilibrated quartz tube still. The flow rate of the argon gas was metered to between 25 and 75 mL/min. An irradiated bismuth target (0.5 mm thick) was wiped dry and placed into a quartz boat. The quartz boat was made from a section of 22 mm o.d. × 180-200 mm quartz glass tubing. The quartz tube still was opened by disconnecting the carrier gas inlet adapter at the standard ball/socket joint end of the still. The quartz boat containing the irradiated target was carefully slid into the center of the quartz tube still. The still was then quickly closed by reconnecting the carrier gas inlet adapter to the still and securing this joint tightly with a ball/socket joint clamp.

The distillation was allowed to proceed for one hour. During the distillation the volume in the reaction vial was maintained by the addition of two 0.25 mL aliquots of MeOH. The distillation was terminated by turning off the furnace and the argon gas flow. A solution of NaHSO₃ (10 uL of a 5.76 mg/mL solution of Na₂S₂O₅ in H₂O, 0.61 umol NaHSO₃) was added to the reaction vial to quench the reaction. The reaction vial was then removed from the quartz tube still by disconnecting the Tefzel ¼-28 thread to female Luer adapter from the Pyrex Luer tip.

The reaction vial was found to contain 75% (988 uCi At-211), decay corrected, of the At-211 originally on the irradiated target while the charcoal trap contained 6% (76 uCi At-211) of the At-211. The reaction vial contents were analyzed by reversed phase C-18 HPLC and shown to contain a mixture of N-succinimidyl oara-[At-211] astatatobenzoate, compound 2, (78%), and oara-[At-211] astatatobenzoic acid (17%). Recovery of injected At-211 from the HPLC column was 92%.

EXAMPLE 2

Antibody Labeling with N-Succinimidyl para-At-2111-astatatobenzoate (2)

A solution containing N-succinimidyl para-[At-211] astatatobenzoate (2) prepared as described in Example 1 was concentrated to dryness by passing a stream of argon gas through the reaction vial for 20 min. To the reaction vial was added 500 uL of a solution containing 200 uL of an antimelanoma murine antibody designated NR-ML-05 (1 mg in PBS), and 300 uL of 1.0 M, pH 9.2 sodium bicarbonate/carbonate buffer. After 10 min at room temperature the crude labeled antibody was purified by gel filtration eluting with PBS to afford the At-211 labeled NR-ML-05 in 35% radiochemical yield. The radiochemical purity of the labeled NR-ML-05 was 98% as assessed by ITLC in 80% methanol.

EXAMPLE 3

Biodistribution Study

Eighteen mice were coinjected with a mixture of NR-ML-05 labeled with N-succinimidyl para-[At-211] astatatobenzoate (2) prepared in an analogous manner as described in Examples 1 and 2, and NR-ML-05 labeled with N-succinimidyl oara-[I-125]iodobenzoate. Groups of six tumor-bearing mice were sacrificed at hour, 4 hours, and 22 hours post injection and the biodistributions of the radiolabels were determined by conventional techniques.

Figure 2A:
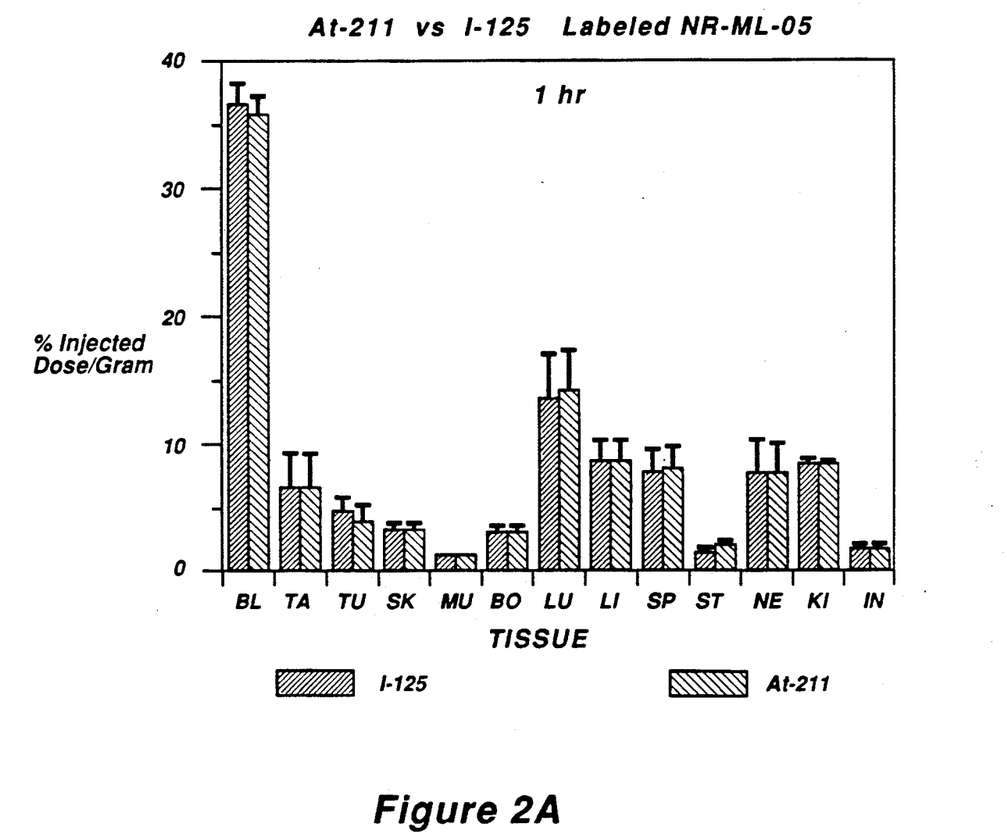
FIGS. 2A–2C present the results of a biodistribution study of an At-211-labeled antibody produced in accordance with the process of the invention.
Figure 2B:
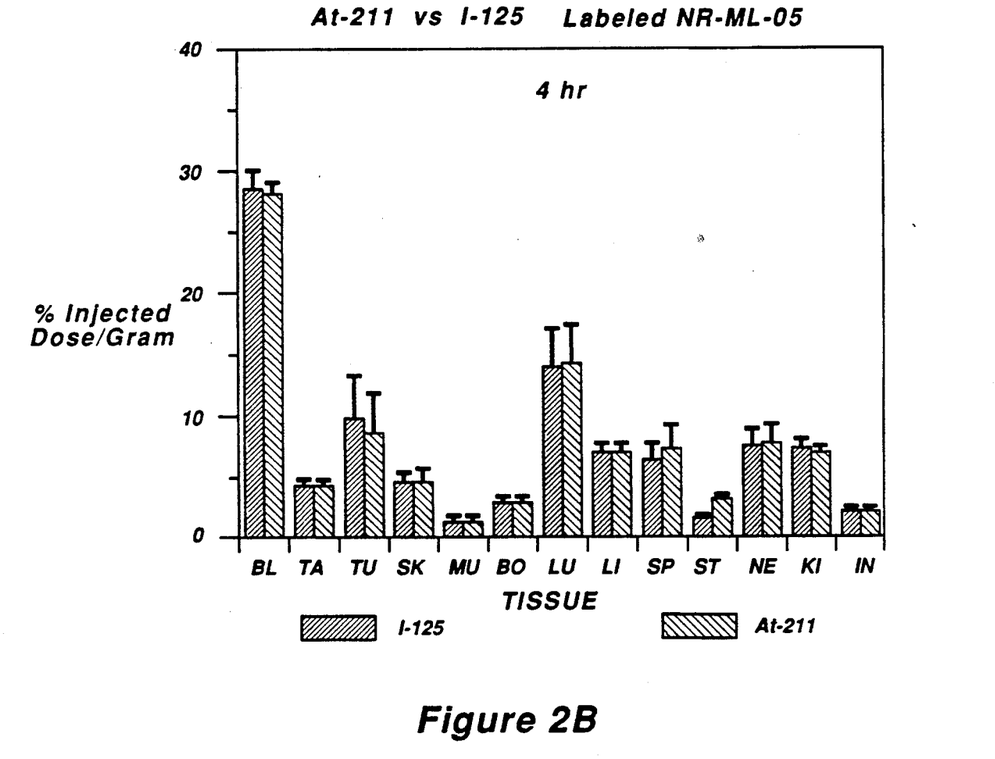
Figure 2C:
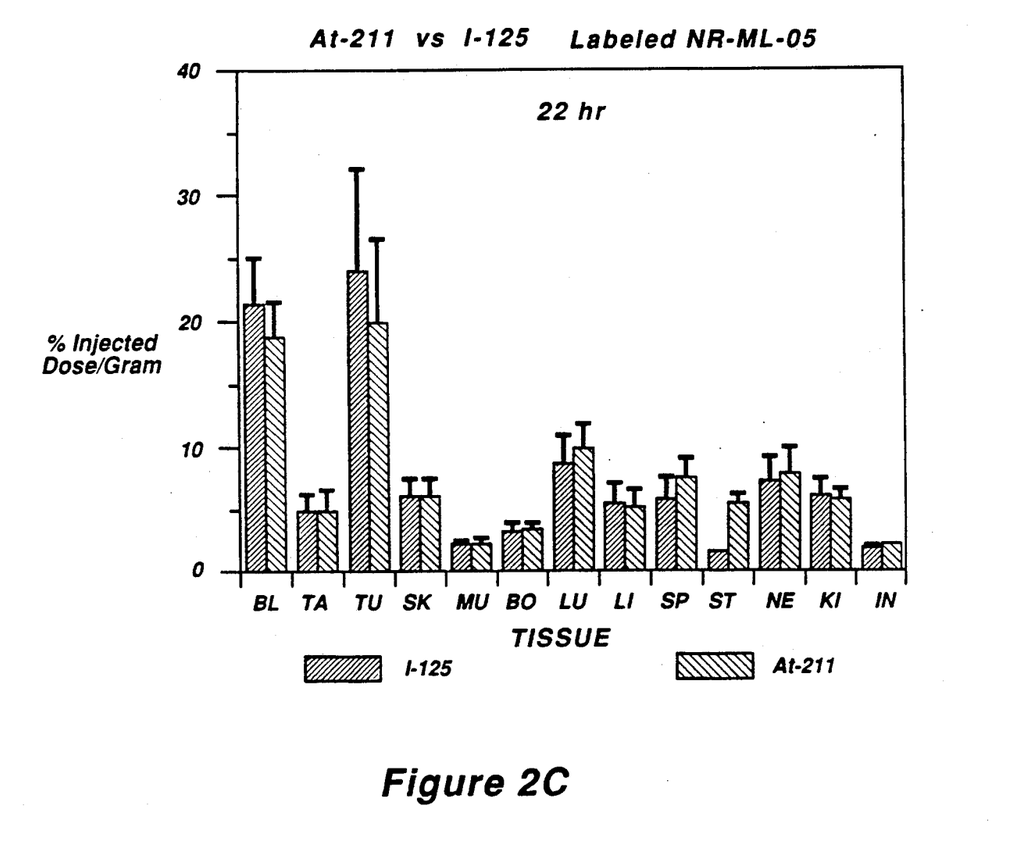

The results are shown as bar graphs in FIG. 2, in which the following symbols are used: BL, blood; TU, antimelanoma tumor; SK, skin; MU, skeletal muscle; BO, bone; LU, lung; LI, liver; SP, spleen; ST, stomach; NE, neck tissue (including thyroid); KI, kidney; and IN, intestine. The results are presented as % injected dose/gram of tissue.

The At-211-labeled antibody was shown to effectively deliver radioactivity to the target tumor. Other targeting proteins can be substituted for the particular monoclonal antibody used in this example.

EXAMPLE 4

Preparation of a 211-At-Labeled Protein Labelling Reagent

In this procedure, the process is conducted under vacuum, without using a carrier gas. An astatine distillation apparatus was set up as depicted in FIG. 3. Trap #3 (u-tube) was cooled with dry-ice/isopropanol (IPA), the vacuum pump was turned on, and the oven was turned on to a setting which would result in reaching a temperature of 700°-720° C. The distilling apparatus was allowed to come to its temperature over approximately one hour. During this time the following reagent solutions were prepared:
(1) 10 mL of a 5% HOAc/MeOH solution
(2) a 1 mg/mL solution of the aryltin reagent (compound 1 shown in example 1) in 5% HOAc/MeOH
(3) A 1 mg/mL solution of N-chlorosuccinimide (NCS) in MeOH
(4) A 0.72 mg/mL solution of Na₂S₂O₅ in H₂O A reaction mixture was prepared using 125 uL of the aryltin reagent solution, 375 uL MeOH, 100 uL N-chlorosuccinimide, and 25 uL PBS.

After approximately one hour, traps #1 and #2 were cooled with dry-ice/IPA. After approximately ten minutes of cooling, the vacuum pump was turned off and argon gas was introduced into the distilling apparatus. Then 425 uL of the prepared reaction mixture was added to trap #1 via the side arm septum on the bottom portion of the trap. After an additional ten minutes of cooling the argon was clamped off and the vacuum pump was turned on. A 200 uL aliquot of the $Na_2S_2O_5$ solution ($NaHSO_3$) was added to trap #2 via the septum at the top.

At this point the irradiated bismuth target was readied for insertion into the distillation apparatus. The vacuum pump was turned off and argon gas was introduced into the apparatus. The large ball joint was opened and the target was placed in a quartz glass boat. Just prior to inserting the target, the pump was turned on (Ar gas clamped off). The target was inserted and the large ball joint was connected and clamped (hard). The distillation was allowed to proceed for approximately 15 minutes, monitoring the activity in trap #1 with an NaI detector. The oven was then turned off.

Figure 4:
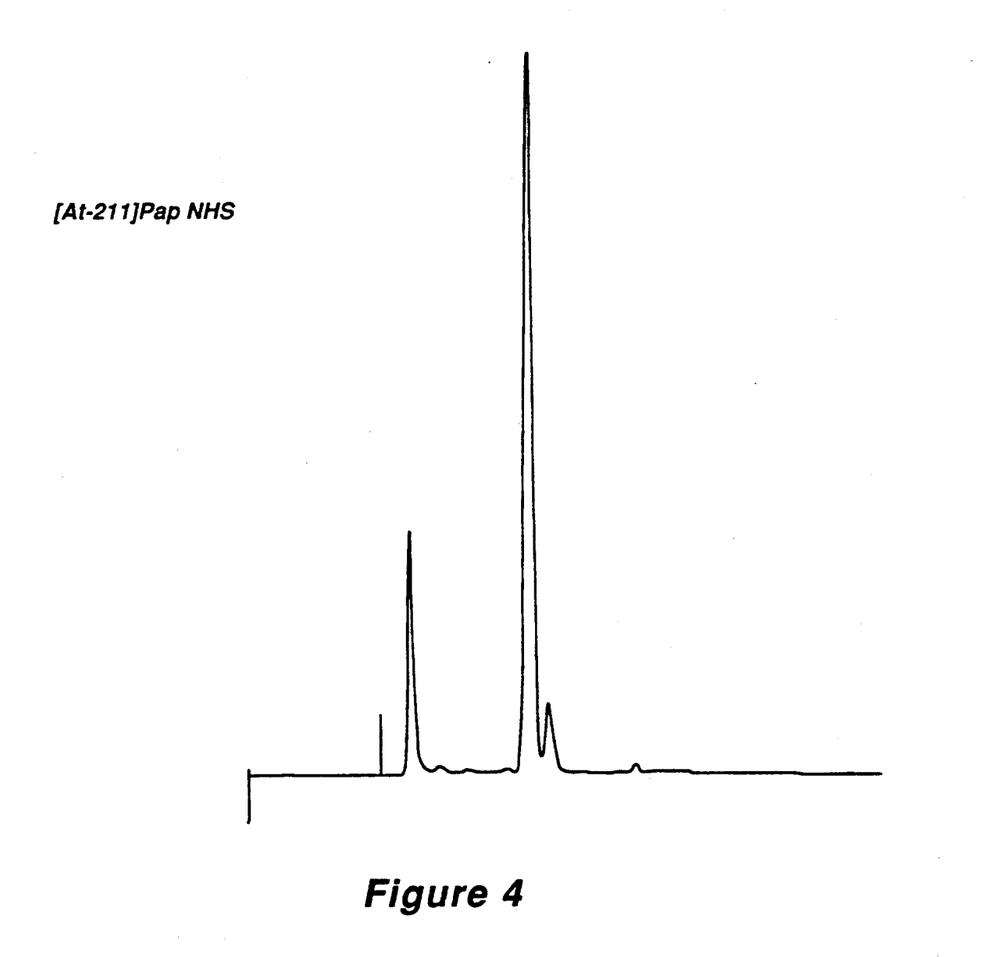
FIG. 4 is a chromatogram showing the reaction products resulting from production of an At-211-labeled radiopharmaceutical compound by the inventive process.

After the 15 minute distilling time the remainder of the reaction mixture (approximately 200 uL) was injected through the septum at the top of trap #1 (to rinse activity down). This was followed by another 200 uL injection of MeOH rinse. The pump was then turned off and argon gas was introduced into the apparatus. The cooling bath under trap #1 was replaced by a warm water bath. After approximately ten minutes, a 200 uL aliquot of the $Na_2S_2O_5$ solution ($NaHSO_3$) was added (with vacuum pump on momentarily) through the septum at the top of the trap. At that point the bottom portion of the first trap was removed and the At-211 was counted in a dose calibrator. The composition of the reaction products was evaluated by radioHPLC of an aliquot of the resultant solution. A representative chromatogram is shown in FIG. 4.

Figure 5:
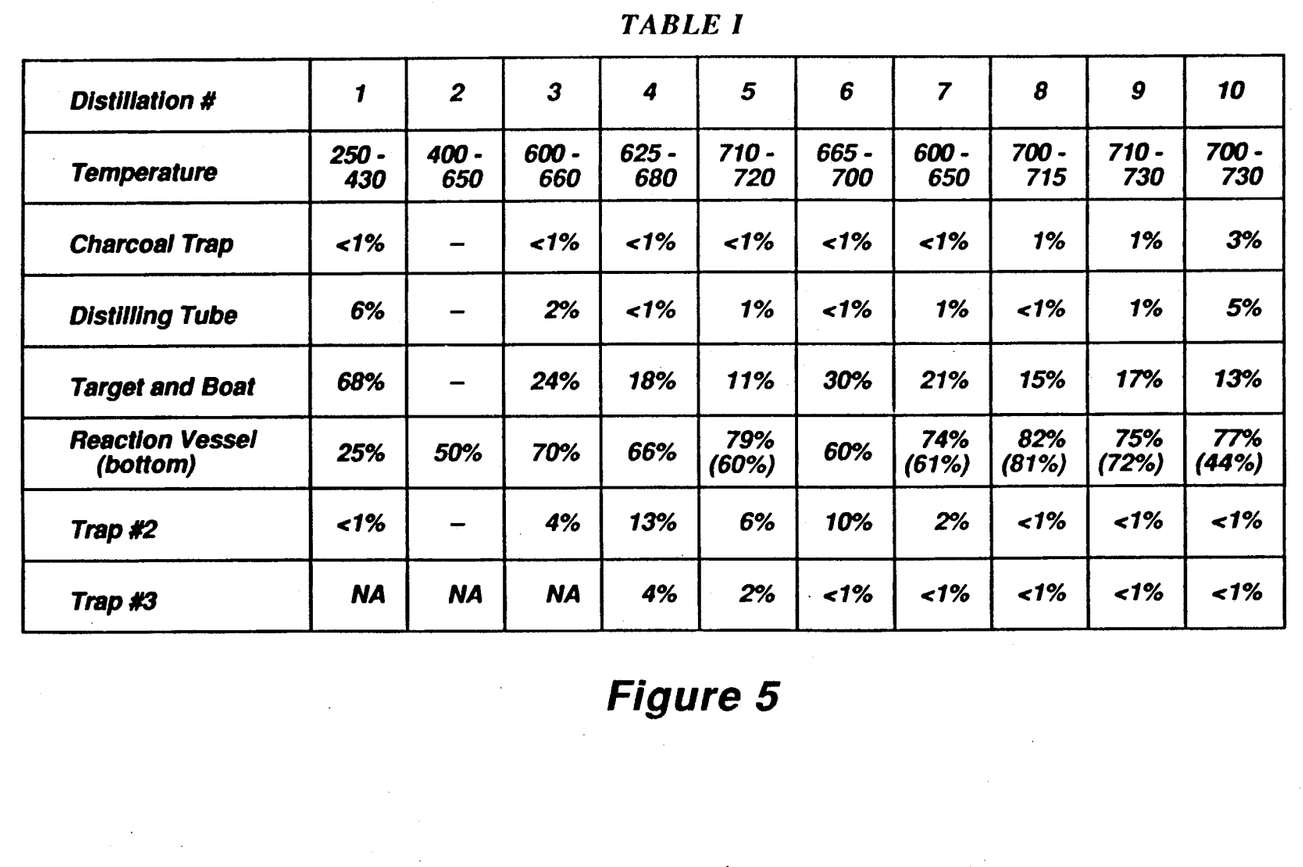
FIG. 5 is a table showing the distribution of radioactivity in a distillation apparatus used in the process of the invention.

FIG. 5 shows the distribution of radioactivity in the distillation apparatus after each of ten runs of this procedure, with variations in temperature as indicated.

EXAMPLE 5

Protein (antibody) labeling with the astatinated protein labeling reagent

Continuing from example 4, the bottom portion of trap #1 was placed back onto the apparatus and the vacuum pump was turned on. A small stream of argon gas was allowed into the apparatus, and the methanol in trap #1 was removed under vacuum (approximately 15 minutes). The vacuum pump was turned off and the apparatus was filled with argon gas. Into trap #1 was added 600 uL of a mixture containing 100 uL of human IgG (2mg) and 500 uL of 0.5M sodium borate buffer.

Figure 6:
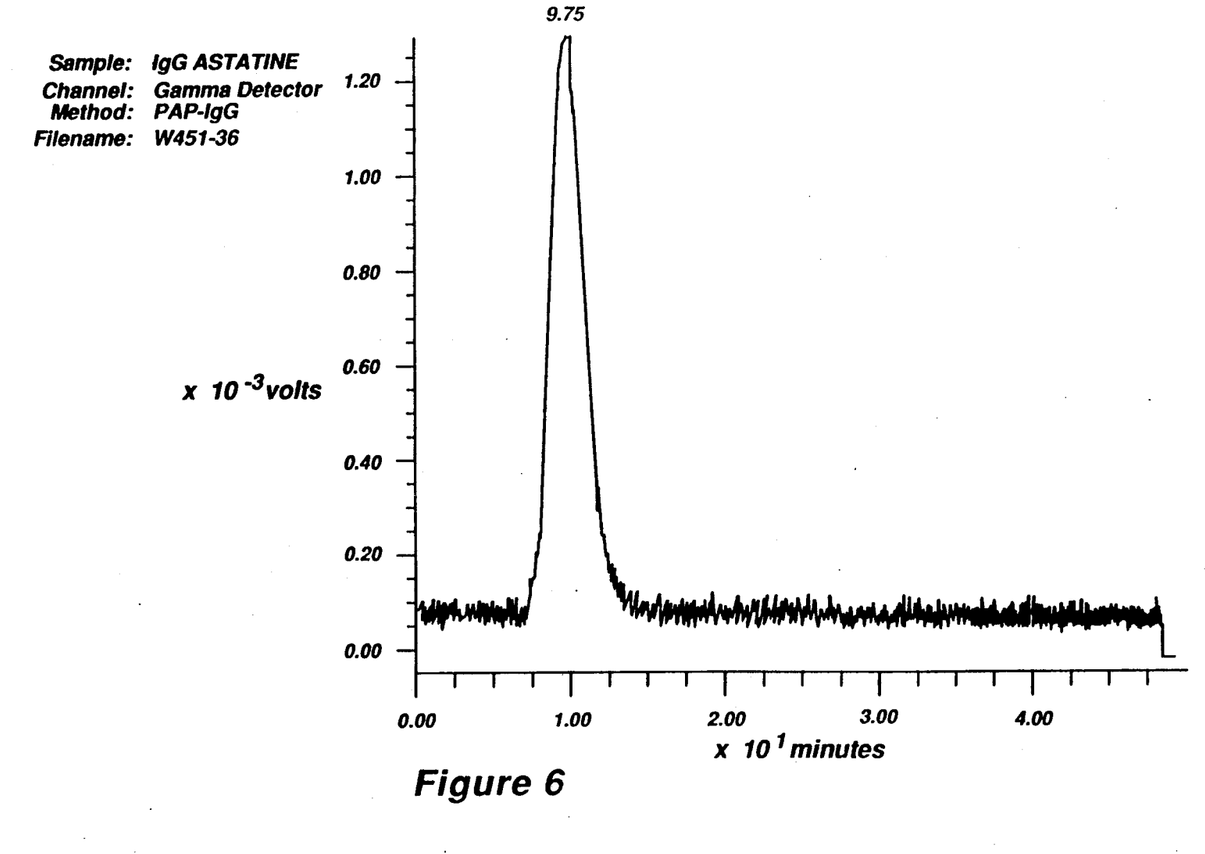
FIG. 6 is an HPLC trace of an At-211-labeled antibody produced by the process of the invention.

The bottom portion of trap #1 was removed after approximately 20 minutes and its contents were poured onto a size exclusion column (PD-10) for purification. One mL fractions were collected, eluting with PBS. The first two tubes contained the desired At-211-labeled antibody. An HPLC trace of the labeled antibody is shown in FIG. 6.

What is claimed is:

1. A process for producing an At-211-labeled radiopharmaceutical compound, comprising
   vaporizing At-211 from an irradiated bismuth metal target, and
   introducing the vaporized At-211 into a solution comprising a compound that binds the At-211 to form an At-211-labeled radiopharmaceutical compound.

2. The process of claim wherein the solution additionally comprises an oxidizing agent.

3. The process of claim 1 wherein the compound that binds the At-211 is a protein labeling reagent.

4. The process of claim 1, wherein the At-211 is vaporized by dry distillation.

5. The process of claim 4 wherein the process is conducted in a single enclosed apparatus under vacuum.

6. The process of claim 4 wherein a carrier gas is used to introduce the vaporized At-211 into the solution.

7. The method of claim 1 wherein the compounds that binds the At-211 is a drug derivatized to contain a metal-containing group that contains a metal selected from the group consisting of tin, germanium, mercury, and boron.

8. The method of claim 7 wherein the metal-containing group is of the formula:

wherein $R_1$, $R_2$, and $R_3$ are each selected from alkyl groups of 1-6 carbon atoms.

9. The process of claim 1 wherein the compound that binds the At-211 is an organic compound comprising a metal-containing group bonded directly to a benzene ring or to a vinyl group,
   wherein the metal-containing group contains a metal selected from the group containing of tin, germanium, mercury and boron.

10. The process of claim 9 wherein the compound is of the formula:

R—Ar—R' wherein
   R represents said metal-containing group,
   Ar represents a benzene ring, and
   R' represents a short-chain substituent of the formula:

wherein n=0-3 and Q represents a conjugation group selected from the group consisting of active esters, amines, hydrazines, and maleimides.

11. The process of claim 9 or 10 wherein the metal-containing group is of the formula:

wherein $R_1$, $R_2$, and $R_3$ are each selected from alkyl groups of 1-6 carbon atoms.

12. The process of claim 11 wherein the radio-pharmaceutical compound is of the formula:

or wherein n=0-3 and Q represents a conjugation group selected fro the group consisting of active esters, amines, hydrazines, and maleimides.

13. A process for recovering At-211 as a radiopharmaceutical compound from an irradiated bismuth metal target, comprising
placing an irradiated bismuth metal target into an enclosed apparatus;
heating the irradiated bismuth metal target for about 10 enclosed apparatus;
heating the irradiated bismuth metal target for about 10-60 minutes at a temperature of from about 650°-750° C., thereby vaporizing the At-211 from the bismuth metal target;
condensing the vaporized At-211 onto a solution comprising an oxidizing agent and a compound that binds the At-211 to form an At-211-labeled radiopharmaceutical compound, and
recovering the At-211-labeled radiopharmaceutical compound.

14. The process of claim 13 wherein the bismuth metal target is heated at about 700°-720° C. for about 10-15 minutes.

15. The process of claim 13 wherein the process is conducted in a single enclosed apparatus under vacuum.

16. The process of claim 13 wherein a carrier gas is used in condensing the vaporized At-211 onto the solution.

17. The process of claim 13 wherein the compound that binds the At-211 is a protein labeling reagent.

18. The method of claim 13 wherein the compound that binds the At-211 is a drug derivatized to contain a metal-containing group that contains a metal selected from the group consisting of tin, germanium, mercury, and boron.

19. The method of claim 18 wherein the metal-containing group is of the formula wherein $R_1$, $R_2$, and $R_3$ are each selected from alkyl groups of 1-6 carbon atoms.

20. The process of claim 13 wherein the compound that binds the At-2311 is an organic compound comprising a metal-containing group bonded directly to a benzene ring or to a vinyl group,
wherein the metal-containing group contains a metal selected from the group consisting of tin, germanium, mercury, and boron.

21. The process of claim 20 wherein the compound is of the formula:

wherein
R represents said metal-containing group,
Ar represents a benzene ring, and
R' represents a short-chain substituent of the formula:

wherein n=0-3 and Q represents a conjugation group selected from the group consisting of active esters, amines, hydrazines, and maleimides.

22. The process of claim 20 or 21 wherein the metal-containing group is of the formula:

wherein $R_1$, $R_2$, and $R_3$ are each selected from alkyl groups of 1-6 carbon atoms.

23. The process of claim 21 wherein the radio-pharmaceutical compound is of the formula:

wherein n=0-3 and Q represents a conjugation group selected from the group consisitng of active esters, amines, hydrazines, and maleimides.

* * * * *

UNITED STATES PATENT AND TRADEMARK OFFICE
CERTIFICATE OF CORRECTION

PATENT NO. : 5,102,651
DATED : April 7, 1992
INVENTOR(S) : Wilbur et al.

It is certified that error appears in the above-indentified patent and that said Letters Patent is hereby corrected as shown below:

In column 12, line 1 [claim 2], before "wherein" and after "claim" please insert --1--.

In column 12, line 11 [claim 7], please change "compounds" to --compound--.

In column 12, line 20 [claim 8], the portion of the formula reading
    Sa    should read    Sn In column 12, line 32 [claim 9], please delete "containing" and insert --consisting-- therefor.

In column 12, line 55 [claim 11], the portion of the formula reading
    Sa    should read    Sn In column 13, lines 19-20 [claim 13], please delete lines 19 and 20

In column 13, line 52 [claim 19], the portion of the formula reading
    Sa    should read Sn In column 13, line 58 [claim 20], please change "At-2311" to --At-211--.

In column 14, line 8 [claim 21], please change "R-Ar-R+" to --R-Ar-R'--.

UNITED STATES PATENT AND TRADEMARK OFFICE
CERTIFICATE OF CORRECTION

PATENT NO. : 5,102,651

DATED : April 7, 1992

INVENTOR(S) : Wilbur et al.

It is certified that error appears in the above-indentified patent and that said Letters Patent is hereby corrected as shown below:

In column 14, line 28 [claim 22], the portion of the formula reading
    Sa    should read    Sn In column 14, lines 40-54 [claim 23], please delete the formulas from line 40 to line 54 and insert the following formula:

or

Signed and Sealed this

Twenty-first Day of November, 1995

Attest:

BRUCE LEHMAN

Attesting Officer    Commissioner of Patents and Trademarks